United States Patent
Sia

(10) Patent No.: US 12,186,220 B1
(45) Date of Patent: Jan. 7, 2025

(54) STIMULATING FOOT BRACE

(71) Applicant: Joseph B Sia, Clifton, NJ (US)

(72) Inventor: Joseph B Sia, Clifton, NJ (US)

( * ) Notice: Subject to any disclaimer, the term of this patent is extended or adjusted under 35 U.S.C. 154(b) by 0 days.

(21) Appl. No.: 18/749,952

(22) Filed: Jun. 21, 2024

(51) Int. Cl.
*A61F 5/01* (2006.01)
*A61H 23/02* (2006.01)

(52) U.S. Cl.
CPC ............ *A61F 5/0113* (2013.01); *A61H 23/02* (2013.01); *A61H 2201/10* (2013.01); *A61H 2201/1642* (2013.01); *A61H 2201/165* (2013.01); *A61H 2205/12* (2013.01)

(58) Field of Classification Search
CPC ......... A61F 5/0113; A61F 5/01; A61H 23/02; A61H 2201/10; A61H 2201/165; A61H 2201/12; A61H 1/00; A61H 1/0237; A61H 1/0266; A61H 2001/027; A61H 3/00; A61H 23/00; A61H 2205/125; A43B 7/146; A43B 3/34; A43B 7/18; A43B 7/20; A43B 7/22; A43B 5/1608; A43B 3/26
USPC .......................................................... 601/21
See application file for complete search history.

(56) References Cited

U.S. PATENT DOCUMENTS

| | | | | |
|---|---|---|---|---|
| 3,976,059 A | * | 8/1976 | Lonardo | A61F 5/0111 602/28 |
| 5,542,912 A | * | 8/1996 | Hess | A61F 5/0585 128/882 |
| 5,836,899 A | * | 11/1998 | Reilly | A61H 23/0263 36/141 |
| 5,913,838 A | * | 6/1999 | Reilly | A61H 23/02 36/141 |
| 7,614,168 B1 | * | 11/2009 | Zummer | A61H 15/0078 601/126 |
| 8,322,055 B1 | * | 12/2012 | Saint-Cyr | A43B 7/146 36/141 |

(Continued)

FOREIGN PATENT DOCUMENTS

| EP | 3756638 A1 * 12/2020 | ............. A43B 3/001 |
|---|---|---|
| WO | WO-2007068729 A1 * 6/2007 | ............... A43B 3/26 |

(Continued)

OTHER PUBLICATIONS

Machine translation of written description and claims for WO2022185483A1 via espacenet (Year: 2022).*

(Continued)

*Primary Examiner* — Timothy A Stanis
*Assistant Examiner* — Tyler A Raubenstraw
(74) *Attorney, Agent, or Firm* — Michael J. Feigin, Esq.; Feigin and Fridman LLC

(57) ABSTRACT

A foot brace, suitable for being worn on the foot of a user. The foot brace includes a sole adapted to abut a plantar surface of the foot of the user, and a cuff flexibly and fixedly connected to a rear portion of the sole. The cuff is adapted to be disposed about an ankle of the foot of the user. A pair of straps reversibly connect a front portion of the sole to the cuff, and can be tensioned to secure the foot brace to the foot. A wire-bearing channel, terminating in a bore, can be embedded into the brace. Conductive wiring, electrically connected to a power source, is disposed within the wire-bearing channel. The wiring terminates in an electrode disposed within the bore, such that when the foot brace is in use, the electrode engages tissue of the user's foot and provides a DC voltage thereto.

18 Claims, 5 Drawing Sheets

(56) References Cited

U.S. PATENT DOCUMENTS

| | | | |
|---|---|---|---|
| 8,529,484 B2* | 9/2013 | Savard | A61F 5/0127 602/5 |
| 8,808,214 B2 | 8/2014 | Herr et al. | |
| 9,398,970 B1* | 7/2016 | Meyer | A61F 5/0111 |
| 9,480,300 B2* | 11/2016 | McDonnell, Jr. | A43B 3/38 |
| 10,076,460 B2* | 9/2018 | Harry | A61H 39/002 |
| 10,226,082 B2* | 3/2019 | Ellis | A43B 17/026 |
| 11,051,957 B2 | 7/2021 | Einarsson et al. | |
| 11,141,302 B1* | 10/2021 | Franco | A43B 5/08 |
| D1,022,225 S * | 4/2024 | Lei | D24/192 |
| 12,041,981 B2* | 7/2024 | Arciuolo | A41D 13/0015 |
| D1,042,856 S * | 9/2024 | Savard | D24/192 |
| 2004/0260211 A1 | 12/2004 | Maalouf | A61H 23/02 601/70 |
| 2005/0054963 A1* | 3/2005 | Ingimundarson | A43B 13/026 602/5 |
| 2005/0124924 A1* | 6/2005 | Slautterback | A61F 5/0111 602/28 |
| 2006/0036197 A1* | 2/2006 | Liu | A43B 3/34 601/21 |
| 2006/0086004 A1* | 4/2006 | Davis | A43B 7/28 36/43 |
| 2006/0235465 A1* | 10/2006 | Koo | A61H 39/002 606/204 |
| 2006/0270958 A1* | 11/2006 | George | A61F 5/0113 602/23 |
| 2007/0203435 A1* | 8/2007 | Novak | A43B 17/00 601/46 |
| 2009/0105624 A1* | 4/2009 | Warner | A61F 5/0111 602/27 |
| 2010/0262044 A1* | 10/2010 | Siegler | A61F 5/0127 600/592 |
| 2011/0082403 A1* | 4/2011 | Hill | A61F 5/0113 602/28 |
| 2011/0251520 A1* | 10/2011 | Shieh | A43D 1/02 600/587 |
| 2011/0264023 A1* | 10/2011 | Devito | A61F 5/0113 602/27 |
| 2012/0023785 A1* | 2/2012 | Barnes | A61F 5/14 36/141 |
| 2012/0060305 A1* | 3/2012 | Yang | B29D 35/126 12/146 B |
| 2012/0145167 A1* | 6/2012 | Davis | A61F 5/0111 128/882 |
| 2013/0046218 A1* | 2/2013 | Wiggin | A61F 5/0127 602/16 |
| 2013/0138030 A1* | 5/2013 | Wenger | A61F 5/0111 602/28 |
| 2013/0226059 A1* | 8/2013 | Morris | A61F 5/0111 602/27 |
| 2014/0121574 A1* | 5/2014 | Chladek | A61N 1/36003 601/27 |
| 2016/0067075 A1* | 3/2016 | Malinowski | A61F 5/0113 602/28 |
| 2016/0081839 A1 | 3/2016 | Hassel et al. | |
| 2016/0331631 A1* | 11/2016 | Odi | A61H 23/02 |
| 2017/0172782 A1* | 6/2017 | McDonnell, Jr. | A61F 5/0113 |
| 2019/0008693 A1* | 1/2019 | Malinsky | A61F 5/0127 |
| 2019/0192327 A1* | 6/2019 | Sutti | A61H 1/0266 |
| 2019/0374365 A1* | 12/2019 | Wu | A61F 5/0127 |
| 2020/0375470 A1* | 12/2020 | Fu | A43B 3/38 |
| 2020/0375776 A1* | 12/2020 | Thor | A61F 5/14 |
| 2021/0260371 A1 | 8/2021 | Shahriari et al. | |
| 2022/0015496 A1* | 1/2022 | Henrichot | A43B 3/34 |
| 2022/0249267 A1* | 8/2022 | Gramaglia | A61F 5/0113 |
| 2022/0287909 A1* | 9/2022 | Sanchez Solana | G16H 20/60 |
| 2022/0339017 A1* | 10/2022 | Shih | B33Y 10/00 |
| 2023/0000655 A1* | 1/2023 | Thor | A43B 7/20 |
| 2023/0064342 A1* | 3/2023 | Dotson | A61H 9/0007 |
| 2023/0218035 A1* | 7/2023 | Walker | A61H 23/0254 36/141 |
| 2023/0277351 A1* | 9/2023 | Kellum | A61F 5/0111 602/27 |
| 2023/0301813 A1* | 9/2023 | Sia | A61F 5/0113 |
| 2024/0000596 A1* | 1/2024 | Johnson | A61F 5/0113 |
| 2024/0041156 A1* | 2/2024 | Urbanowicz | A43B 7/223 |
| 2024/0099934 A1* | 3/2024 | Stanfield | A41D 13/12 |
| 2024/0139012 A1* | 5/2024 | Thor | A61F 5/0111 |

FOREIGN PATENT DOCUMENTS

| | | | | |
|---|---|---|---|---|
| WO | WO-2020120811 A1 * | 6/2020 | | A43B 13/16 |
| WO | WO-2022185483 A1 * | 9/2022 | | A61F 5/0113 |
| WO | WO-2023186955 A1 * | 10/2023 | | |

OTHER PUBLICATIONS

Machine translation of written description and claims for WO2020120811A1 via espacenet (Year: 2020).*

Machine translation of written description and claims for WO2023186955A1 via espacenet (Year: 2023).*

* cited by examiner

STIMULATING FOOT BRACE

FIELD OF THE DISCLOSED TECHNOLOGY

The disclosed technology relates to stimulating mechanisms for muscular disorders, and more specifically, for vibratory stimulation of adjustable footwear.

BACKGROUND

Drop foot, also known as foot drop, is a debilitating condition characterized by the inability to lift the front part of the foot, leading to dragging of the foot on the ground while walking. This condition can result from various causes, including nerve damage, muscle weakness, neurological disorders, or injuries to the lower leg or foot. Individuals with drop foot often experience difficulty walking, instability, and/or an increased risk of falls, significantly impacting their mobility and quality of life.

Current treatment options for drop foot include physical therapy, orthotic devices such as ankle-foot orthoses (AFOs), and surgical interventions. While these treatments can provide some relief, they often have limitations, including discomfort, restricted mobility, and/or the need for invasive procedures.

There is thus a need in the art for non-invasive, effective, and convenient treatment options for individuals with drop foot pathology.

SUMMARY OF THE DISCLOSED TECHNOLOGY

The disclosed vibratory stimulation device aims to address the limitations of current treatment options for drop foot by providing a non-invasive and non-pharmacological intervention (NPI), which is a portable, and user-friendly solution for individuals with this condition. The device is designed to deliver precise vibration massage to the foot and lower leg, promoting muscle activation to restore normal gait patterns. The trembling movement stimulates soft tissues in the body and can help stimulate nerves, relieve muscular tension, decrease stress, produce a feeling of relaxation, and improve blood circulation.

The vibratory stimulation foot brace of the disclosed technology is designed to alleviate symptoms of drop foot pathology by supporting the foot from bending and/or delivering muscle activation to the foot and bottom leg. The vibratory stimulation action can be generated by, for example, a flat coin button-type micro direct current vibrating motor. The brace comprises several key components designed to fit comfortably within a shoe while ensuring effective stimulation and preventing foot drop.

The core of the device is a ventral sole, contoured to match the curvature of the user's plantar surface. This sole, when worn inside a shoe, aligns its dorsal surface with the plantar surface of the foot and its ventral surface with the sole of the shoe. A calcaneal cuff is connected to the ventral sole and extends upwards along the user's calcaneal tendon, conforming closely to the anatomical curvature of the heel region. This cuff also abuts the interior surface of the shoe to provide stable support.

The brace features at least one rail projection extending upward from the phalangeal region of the ventral sole, enhancing structural support. Embedded within the ventral surface of the sole and the outer surface of the calcaneal cuff is a wire-bearing channel that houses conductive wiring connected to a power source. The vibration mechanism, such as the afore-described flat coin button-type micro vibrating motors, are exposed through bores at the terminal ends of the channels delivering trembling movement to the user's foot and leg, facilitating therapeutic stimulation.

In some embodiments, the device may include additional features to enhance usability and comfort. For example, the brace may have eyelet projections connected to the rail projections, and straps that can be attached through these eyelets to secure the brace. An upper cuff connected to the calcaneal cuff may allow the straps to be secured with hook and loop fasteners, ensuring a snug fit. Flexible connectors may link the rail projections to the eyelets, and the tension from the straps may pull the upper cuff towards the rail projections, causing the upper region of the calcaneal cuff to abut the user's calf muscle, ensuring stability and comfort.

Further structural enhancements may include flanges extending from the lower region of the calcaneal cuff towards the phalangeal region. These flanges may abut both the user's foot and the interior of the shoe, providing additional support.

In some embodiments, the wire-bearing channel is designed to maximize coverage, extending transversely along the majority of the ventral sole and the calcaneal cuff. This channel may branch off to terminate at multiple bores, ensuring effective distribution of vibratory stimulation across the foot, heel, and bottom leg. In certain configurations, these branches and sub-branches ensure precise targeting of specific areas for optimal therapeutic benefits.

Overall, the vibratory stimulation foot brace offers a comprehensive solution for managing drop foot, combining structural support with advanced vibratory stimulation to enhance the relieve of muscular tension, decrease stress, produce a feeling of relaxation, and improved blood circulation for the user.

DETAILED DESCRIPTION OF EMBODIMENTS OF THE DISCLOSED TECHNOLOGY

The vibratory stimulator foot brace of the disclosed technology is designed to strengthens the muscle fibers and improves balance, thereby reducing fall risk. Vibratory stimulating creates significant improvements in reaction time, movement velocity and quadricep muscle strength. The devices can further be used in fall prevention programs, alongside other interventions such as exercises. The vibratory stimulation generates a "low-intensity vibration" (LIV therapy) which offers a safe and accessible solution.

The low intensity vibration releases a tiny (defined as, "less than enough to force movement of a limb of an average human") "up and down vibrations" which travel through the feet, up the legs, into the hip and lower spine. Low intensity vibration gently stimulates the body. These precise movements of Low-intensity Vibrations (LIV) encourage the body's bone-forming cell to work. It is a safe and natural way to improve bone health. The methods and devices disclosed herein use non-pharmacological interventions for the management of chronic health conditions and concommunicable diseases known as "NPIs". NPIs products, methods, programs or services are linked to biological and/or psychological processes identified in clinical studies".

A battery used to provide current to the device can be a rechargeable Li-on 3.7 volts small battery. The battery may be used for hours before being the need to be recharged.— The brace comprises several key components designed to fit comfortably within a shoe while ensuring effective stimulation. The material of the AFO is of flexible type using TPU filament made from thermoplastic polyurethane and semi-flexible type made with Polypropylene (PP) filament.

The device includes a ventral sole, contoured to match the curvature of the user's plantar surface. A calcaneal cuff is connected to the ventral sole and extends upwards along the user's calcaneal tendon, conforming closely to the anatomical curvature of the heel region. This cuff also abuts the interior surface of the shoe to provide stable support. The device further includes a brace featuring at least one rail projection extending upward from the phalangeal region of the ventral sole, enhancing structural support. Embedded within the ventral surface of the sole and the outer surface of the calcaneal cuff is a wire-bearing channel that houses conductive wiring connected to a power source. The motors (e.g. flat coin button-type vibrating motors) are exposed through bores at the terminal ends of these channels deliver a low-intensity vibration to the user's foot and lower leg, facilitating the low intensity vibration (LIV) therapeutic stimulation.

Embodiments of the disclosed technology will become clearer in view of the following discussion of the figures.

Figure 1:
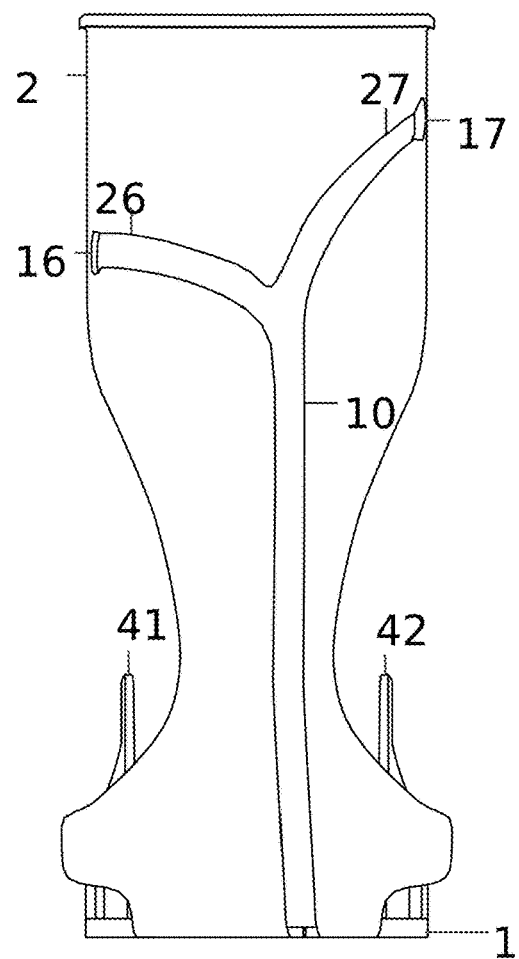
FIG. 1 is a rear plan view of a vibratory stimulator foot brace in an embodiment of the disclosed technology.

FIG. 1 is a rear plan view of a vibratory stimulation foot brace 100 in accordance with an embodiment of the disclosed technology.

As seen, the foot brace 100 includes a ventral sole 1 and a calcaneal cuff 2, which are fixedly connected to one another.

For purposes of this disclosure, two components are said to be "fixedly connected" to one another if, whilst the two connected components undergo typical forces associated with their intended use, the two components remain affixed to one another (thereby forming a contiguous structure), such that when a first one of the components is lifted from a base surface, the second component remains connected to, and is lifted together with, the first component. This is in contrast to two components that "abut" one another, denoting that a subsection of any face or surface of a first component and a second component respectively physically contact one another. The nature of the contact of "abutment", however, is that the two components described to abut one another are separable from one another, only touching one another, such that when a first one of the components is lifted fully from a base surface, the second component detaches from the first component.

Figure 7:
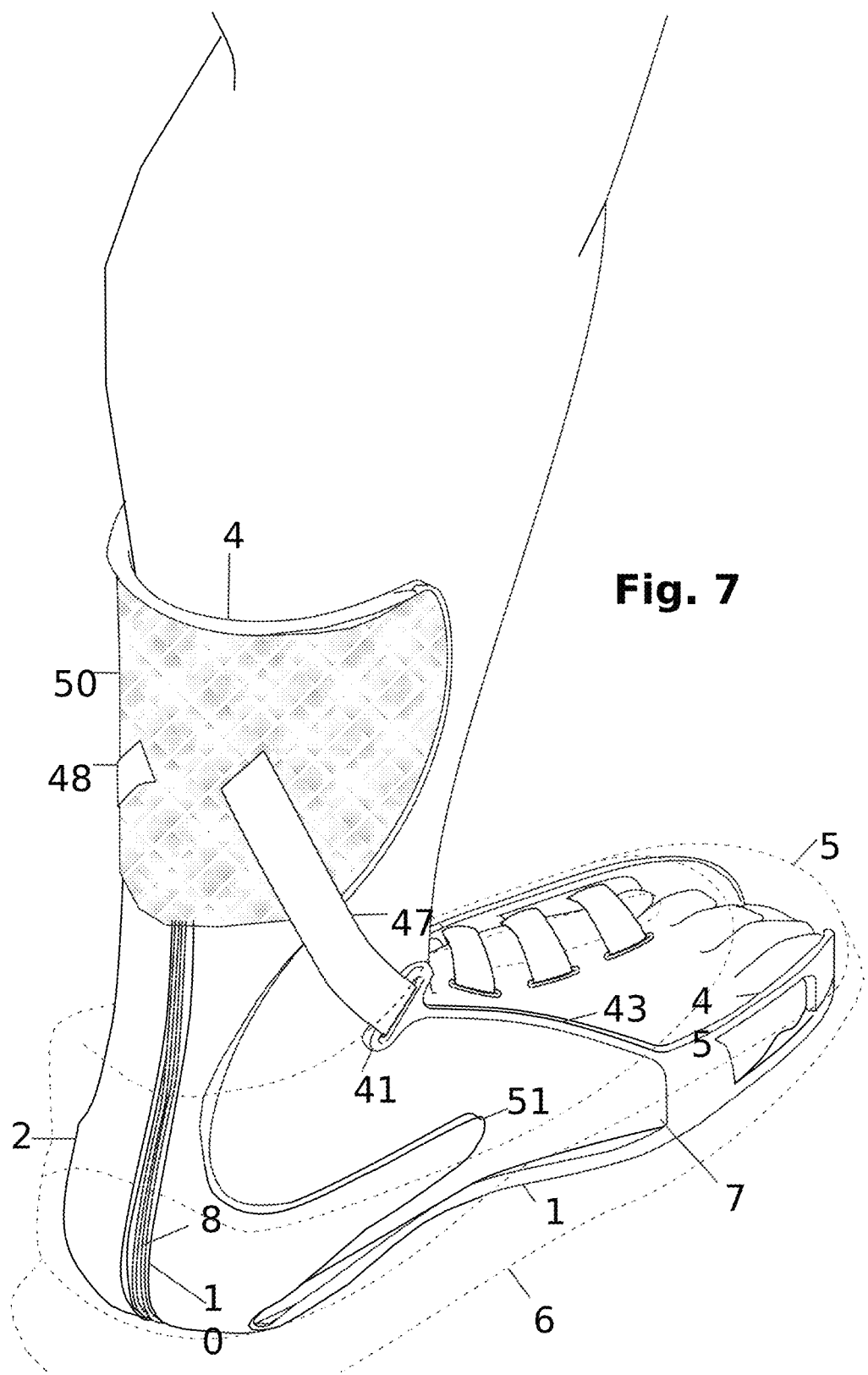
FIG. 7 is a top and left perspective view of a vibratory stimulator foot brace in an embodiment of the disclosed technology, when worn on the foot of a user within a shoe.

When foot brace 100 is in use by a user, it is typically placed within a shoe 5, such that ventral sole 1 abuts a dorsal region of a sole 6 of the shoe 5 (see FIG. 7). As such, contact between ventral sole 1 and sole 6 of shoe 5 ceases upon lifting of the foot brace relative to shoe 5, for intended removal of the brace from the shoe interior. In some embodiments, ventral sole 1 is contoured to a curvature of a plantar surface of a foot of the user.

Figure 2:
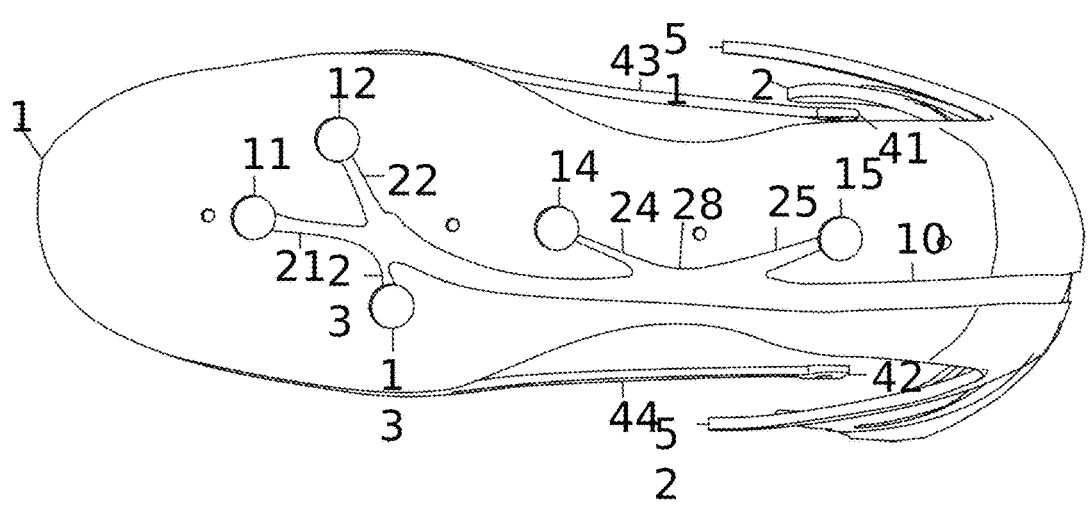
FIG. 2 is a bottom plan view of a vibratory stimulator foot brace in an embodiment of the disclosed technology.
Figure 3:
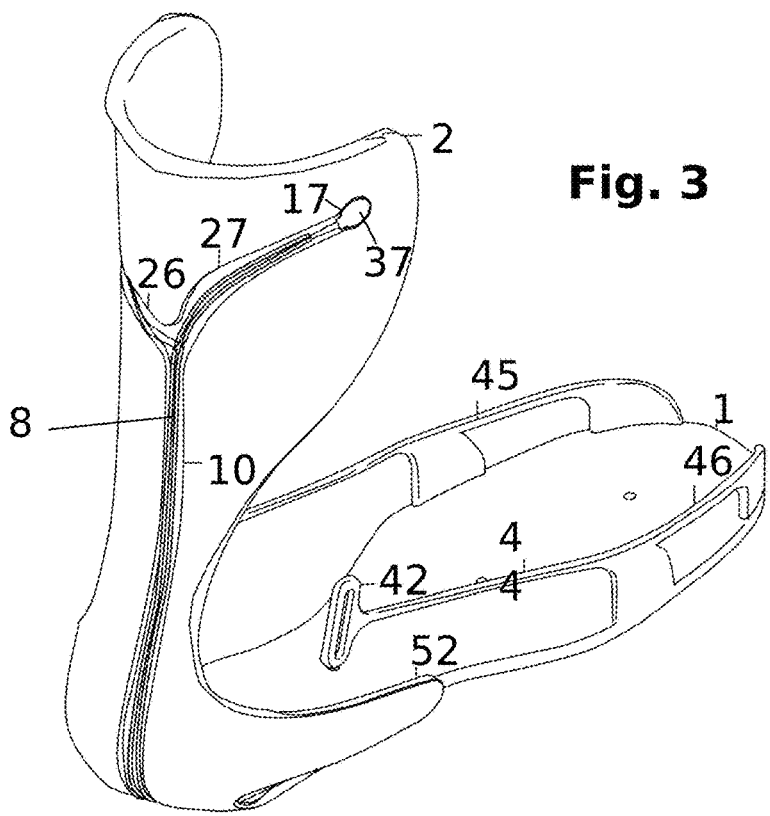
FIG. 3 is a rear and left side perspective view of a vibratory stimulator foot brace an embodiment of the disclosed technology.

Foot brace 100 further includes a wire-bearing channel 10 in FIG. 1, FIG. 2, FIG. 3, FIG. 4 terminating, at least one end thereof, in a bore extending a surface of foot brace 100. FIG. 1 shows a branching structure of channel 10 in FIG. 1, FIG. 2, FIG. 3, FIG. 4 in an embodiment of the disclosed technology, including a first branch 26 in FIG. 1 and FIG. 3 terminating at a bore 16 in FIG. 1, and a second branch 27 in FIG. 1 and FIG. 3 terminating at a bore 17 in FIG. 1 and FIG. 3, branching off from the main channel in FIG. 1, FIG. 2, FIG. 3, FIG. 4. In the illustrated embodiment, bores 16 and 17 in FIG. 1 extending through cuff 2. In some embodiments, bore 17 in FIG. 1 and FIG. 3 at the terminus of second branch 27 in FIG. 1 and FIG. 3 may be located at a lateral region of the calcaneal cuff 2, whilst bore 16 in FIG. 1, at the terminus of a first branch 26 in FIG. 1 and FIG. 3 may terminate at a medial region of the cuff. The lateral and medial regions are both defined with relation to a foot of a user of the device whilst the device is in ordinary use as designed by the manufacturer, e.g. the medial region of the calcaneal cuff 2 in FIG. 1 and FIG. 3 is the area thereof more proximal to the hallux than to the pinky toe, whilst the lateral region of the calcaneal cuff 2 is the area thereof that is more proximal to the pinky toe than to the hallux.

FIG. 2 is a bottom plan view of a vibratory stimulation foot brace in accordance an embodiment of the disclosed technology. In some embodiments of the disclosed technology, and as illustrated, ventral sole 1 may be shaped substantially in the silhouette of a sole of a shoe, or of the bottom/plantar surface of a foot. However, in some other embodiments, ventral sole 1 may have a different shape, such as an oval or rectangular shape.

As seen in FIG. 2, channel 10 extends from cuff 2 into sole 1, and forms multiple branches. In the illustrated embodiment, the main channel includes a first branching point 20 in FIG. 6, and a second branching point 28. From branching point 20, split channel branches 21, 22, and 23 in FIG. 2, terminating at bores 11, 12, and 13 in FIG. 2, respectively. From branching point 28 in FIG. 2, split channel branches 24 and 25 in FIG. 2, terminating at bores 14 and 15 in FIG. 2, respectively. In the illustrated embodiment, branch 21 in FIG. 2 substantially continues substantially forwardly from main branch 10 in FIG. 2, branch 22 in FIG. 2 extends to a medial region of sole 1 in FIG. 2, and branch 23 in FIG. 2 extends to a lateral region of sole 1. Both of branches 24 and 25 in FIG. 2 extend from branch 10 and from branching point 28 to the medial region of sole 1, such that branch 25 in FIG. 2 extends toward a rear region of the sole, and branch 24 in FIG. 2 extends toward a forward region of the sole.

The rear and forward regions are both defined with relation to a foot of a user of the device while the device is in ordinary use as designed by the manufacturer. The forward region of sole 1 is the area thereof more proximal to the toes than to the heel, while the rear region of sole 1 is the area thereof that is more proximal to the heel than to the toes.

In some embodiments, the channel 10 in FIGS. 1, 2, 3 and 4 extends along a majority of a longest dimension of ventral surface of the ventral sole 1 and along a majority of a longest dimension of an outer surface of the calcaneal cuff 2, the channel 10 being indented into these respective surfaces.

The wiring and flat coin vibrating motors that occupy the channel 10 and its branches 21, 22, 23, 24, 25, 26, and 27, as well as bores 11, 12, 13, 14, 15, 16, and 17, are described in further detail herein-below with respect to FIGS. 3 and 4.

FIG. 3 is a rear and left side perspective view of vibratory stimulation foot brace 100 in accordance with an embodiment of the disclosed technology. FIG. 4 is a bottom left perspective view of vibratory stimulation foot brace 100 in accordance with an embodiment of the disclosed technology. As seen in FIGS. 3 and 4, wiring 8 is accommodated within channel 10 in FIGS. 1, 2, 3, 4 and 7. Wiring 8 in FIG. 4 and FIG. 7 is adapted to deliver from a power source such as battery 9, which in some embodiments may be embedded within the foot brace body. In the shown embodiment, the mini-vibration motors are disposed at termini of wiring 8. As explained in further detail herein, the mini vibration motors are disposed within respective ones of bores 11 (see FIG. 2)-17 (see FIG. 3) at termini of channel 10, and are adapted to deliver electricity from wiring 8 (see FIG. 4) to the body of a wearer of brace 100.

Figure 4:
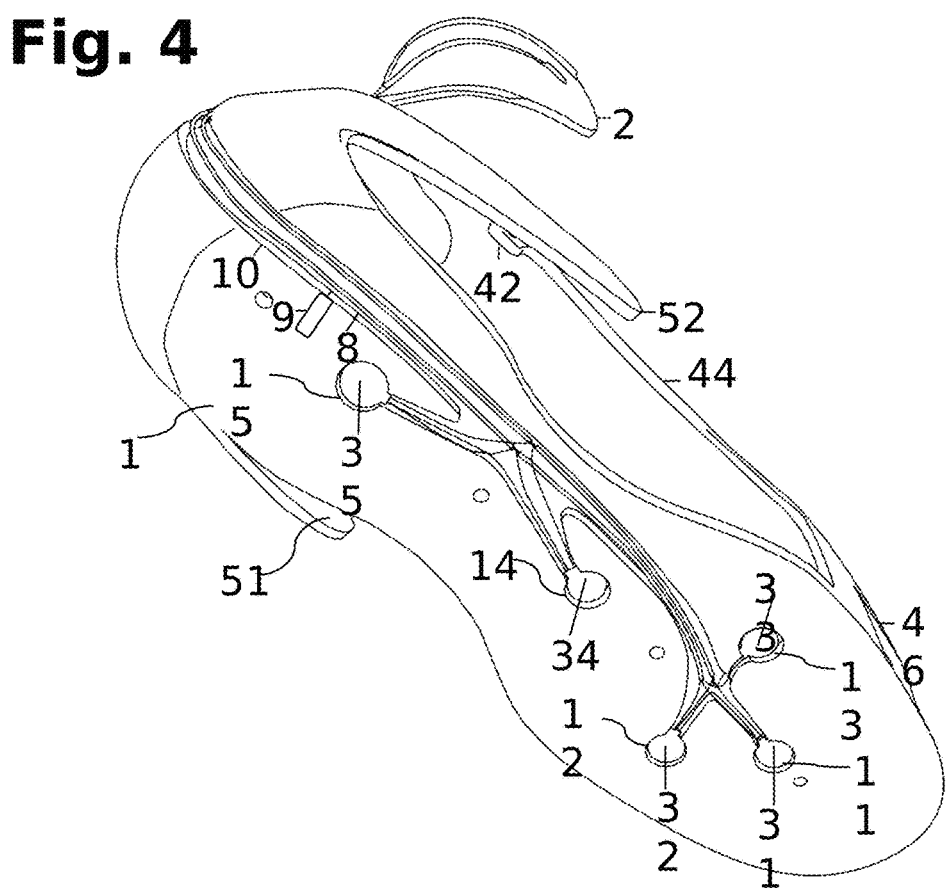
FIG. 4 is a bottom and left perspective view of a vibratory stimulator foot brace in an embodiment of the disclosed technology.

Specifically, The mini vibration motor 31 in FIGS. 4 and 2 is accommodated within bore 11 at the terminus of branch 21 of channel 10. The mini vibration motor 32 in FIGS. 4 and 2 is accommodated within bore 12 at terminus of branch 22. The mini vibration motor 33 in FIGS. 4 and 2 is accommodated within bore 13 at terminus of branch 23. The mini vibration motor 34 in FIGS. 4 and 2 is accommodated within bore 14 at terminus of branch 24. The mini vibration motor 35 in FIGS. 4 and 2 is accommodated within bore 15 at terminus of branch 25. The mini vibration motor 36 in FIG. 1 is accommodated within bore 16 at terminus of branch 26 also in FIG. 3. The mini vibration motor 37 in FIG. 3 is accommodated within bore 17 at terminus of branch 27 also in FIG. 1.

Rail projections 45 and 46 in FIG. 3 are fixedly connected to a phalangeal region of an outer curvilinear edge of the ventral sole 1, such that one extends along the medial edge of the sole and the other extends along the lateral edge of the sole. Rail projections 45 and 46 extend upwardly from the ventral sole 1, substantially perpendicularly thereto. The "phalangeal region" (FIG. 6, 20) is defined as the frontal area of the foot, wherein the majority of the underlying bone is phalangeal. Rail projections 45 and/or 46 may also be fixedly connected to a portion of the outer edge of the ventral sole 1 that is adjacent to the metatarsals, along the respective medial and/or lateral edges.

An elongated flexible connector 43 in FIG. 2 extends from rail projection 45 in FIG. 3 and terminates, at an end thereof distal to the rail projection, in an eyelet projection 41 in FIG. 2. Similarly, an elongated flexible connector 44 extends from rail projection 46 and terminates, at an end thereof distal to the rail projection, in an eyelet projection 42 in FIG. 2.

In some embodiments, flanges 51 in FIGS. 4 and 52 in FIG. 4 extend from the lower calcaneal cuff 2 towards the phalangeal region, and toward rail projections 45 and/or 46 in FIG. 3.

Figure 5:
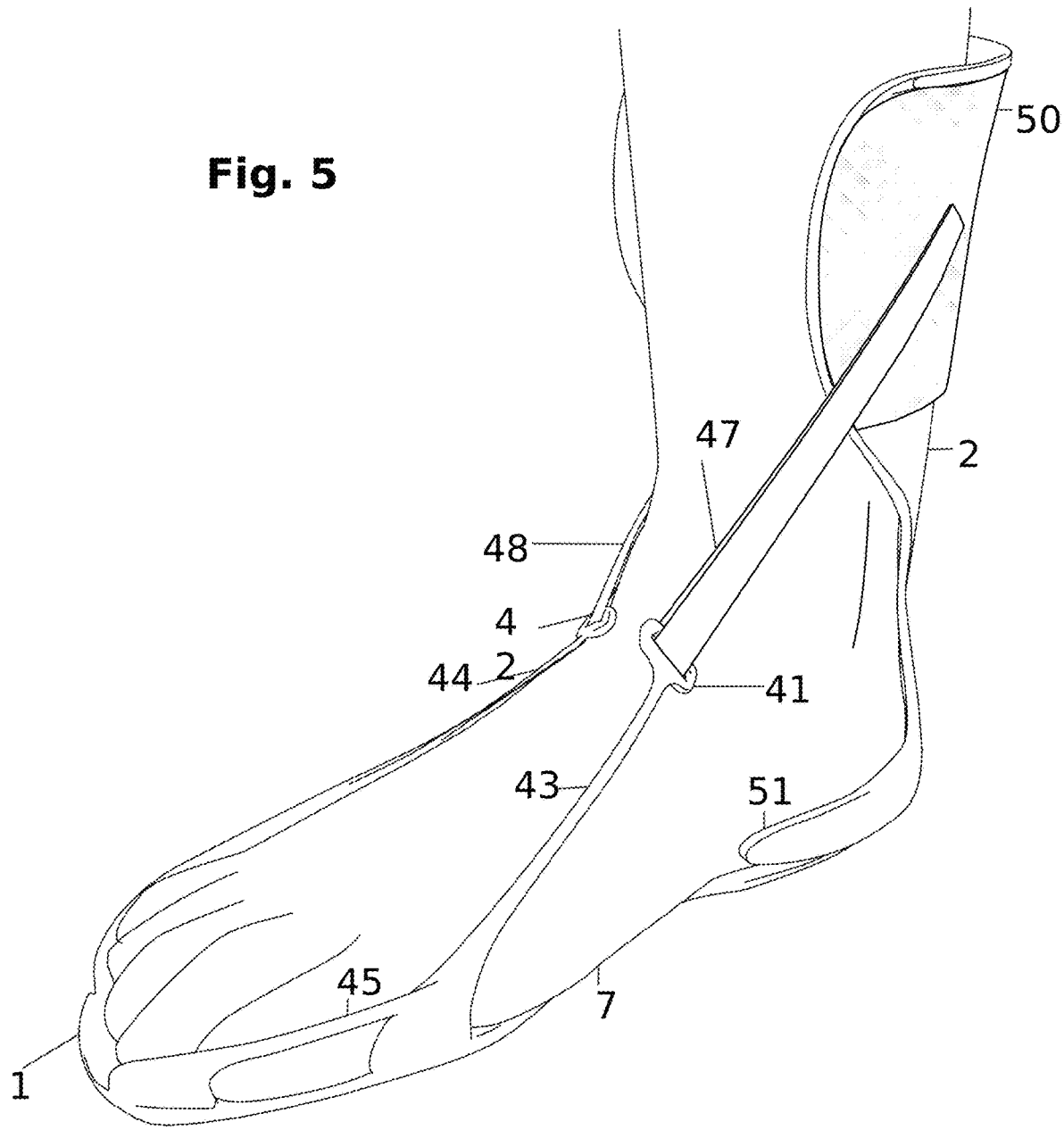
FIG. 5 is a top and right perspective view of a vibratory stimulator foot brace in an embodiment of the disclosed technology, when worn on the foot of a user.

FIG. 5 is a top right perspective view of vibration stimulating foot brace 100 worn on the foot of a user in an embodiment of the disclosed technology. As seen in FIG. 5, flanges 51 and 52 in FIG. 4 abut foot 7 in FIG. 5 in a region whose nearest bone is the heel/calcaneus bone, and the flanges stretch therefrom towards the phalangeal region. As seen, flange 51 is disposed on a medial side of the foot and of brace 100, while flange 52 in 54 is disposed on a lateral side of the foot and brace. Additionally, rail projections 45 and 46 abut the phalangeal region 20 of foot 7, on the medial and lateral sides of the foot, respectively. The abutment of flanges 51 and 52 and foot 7 assists in securing brace 100 to the foot of the user, as does the abutment of the rail projections 45 and 46 and the phalangeal region 20.

Further securement of the brace device to the foot 7 may be achieved by an upper cuff 50 fixedly connected to an upper region of the calcaneal cuff 2 of brace 100. In some embodiments, upper cuff 50 may interface with straps 47 and 48, for example via a hook and loop fastener mechanism, or using any other fastening mechanism (e.g., snaps, hooks and eyes, buttons, and the like). In some embodiments, and as illustrated, straps 47 and 48 loop through eyelet projections 41 and 42 respectively, while ends of the straps are affixed to the hook and loop fastener of the upper cuff 50. Tension applied to straps 47 and 48 may assist in keeping the straps taut, thereby further securing brace 100 to the foot. In some embodiments, elongated flexible connectors 43 and 44 may have sufficient elasticity, so as to be further elongated by tension applied thereto. In some embodiments, tension of straps 47 and 48 acting on eyelet projections 41 and 42 pulls connectors 43 and 44 towards the upper cuff 50, further stretching the connectors and increasing an angle of elevation between ventral sole 1 and connectors 43 and 44.

The two flanges 51 and 52 shown in the figures extend from the calcaneal cuff, in addition on providing lateral support to the coot brace from both sides. Those flanges leave the sole of the foot brace free to bend upwards (more acutely towards the vertical/calf section of the brace) to apply pulling force until the wings are touching the base reaching 70 degrees upwards compared to the linear extent of the sole. This possibility allows the individual to practice exercises to reinforce the foot muscles. Also, by having the sole free from any lateral support, in embodiments of the disclosed technology, the foot is movable in directions of pronation, supination, flexion and extension while wearing the brace.

Typically, straps 47 and 48 are selectively detachable from upper cuff 50, and thus also from calcaneal cuff 2, for example by detachment of the hook and loop fastener mechanism. Such detachment may be useful, for example, for removal of brace 100.

For removal of brace 100, the user may selectively detach the straps 47 and 48 from upper cuff 20, thereby releasing the tensional forces securing the brace to foot 7. In some embodiments, the user may selectively entirely remove straps 47 and 48 from eyelet projections 41 and 42.

While securing the brace, a user may choose from a variety of points along the upper cuff 50 to which to selectively attach or adhere straps 47 and 48. The farther a point of attachment of straps 47 and 48 to upper cuff 50 is from phalangeal region 20, the tauter the straps will be, resulting in greater tensional forces securing the brace onto foot 7 of the user.

Figure 6:
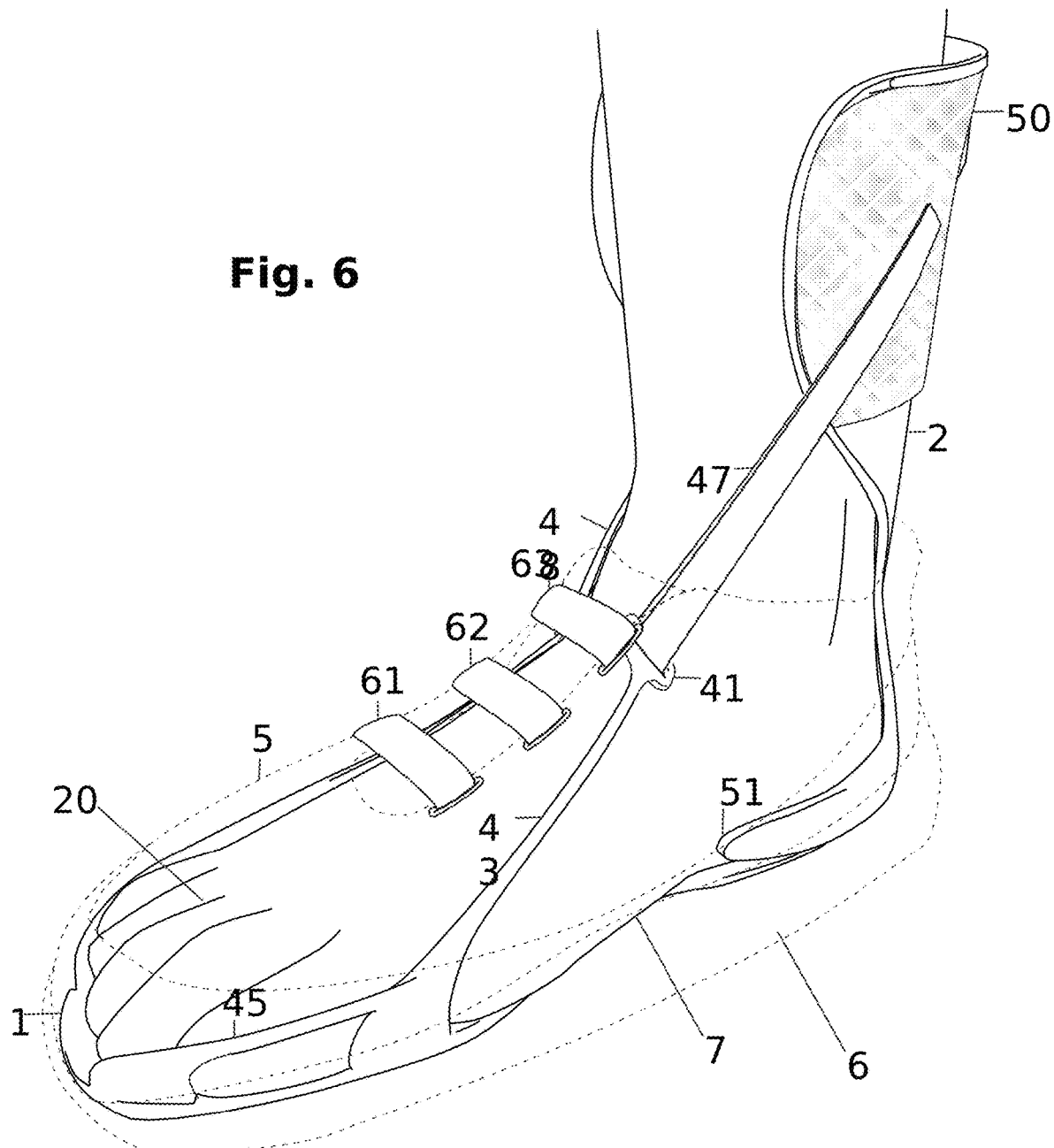
FIG. 6 is a top and right perspective view of a vibratory stimulator foot brace in an embodiment of the disclosed technology, when worn on the foot of a user within a shoe.

FIG. 6 is a top and right perspective view of vibration stimulating foot brace 100, while worn on foot 7 of the user within shoe 5, in accordance with an embodiment of the disclosed technology. While brace 100 is disposed within shoe 5, one or more components of the brace may abut the interior of the shoe. For example, rail projections 45 and 46 may abut medial and lateral side surfaces of the shoe, at least a portion of calcaneal cuff 2 may abut a heel portion of the shoe, and ventral sole 1 may abut the sole of the shoe. The abutment of brace 100 against the interior of shoe 5 and/or against foot 7 may result in frictional or compressional forces, further securing the brace in place whilst mitigating movement of the brace with respect to foot 7.

Fastening mechanisms of the shoe 5 itself, such as tight enable straps-61, 62, and 63, or shoelaces (not explicitly shown) may further secure the positioning of brace 100 with respect to shoe 5. The weight born by foot 7 standing on ventral sole 1 may push ventral sole 1 downwards against sole 6 of shoe 5, contributing to the abutment of the two soles against one another.

FIG. 7 is a top and left perspective view of vibration stimulating foot brace 100 worn on the foot of a user inside a shoe in accordance with an embodiment of the disclosed technology. Tension of straps 47 and 48 and of flexible connectors 43 and 44 may pull calcaneal cuff 2 against the calf muscle of the user, creating a region 4 where the cuff abuts the calf muscle. This abutment may facilitate contact of electrodes within the calcaneal cuff 2, such as electrodes 16 and 17, with the body of the user, for stimulation of muscles thereof. The calcaneal cuff 2 is so named, as it runs upwards from the calcaneus bone along the calcaneal tendon, although the edges of cuff 2 may stretch farther around the circumference of the leg than does the calcaneal tendon.

It is to be appreciated that, while brace 100 is shown as being suitable for, and being worn on, a left foot of a user, an identical or mirror image brace may be used for the right foot of the user, simultaneously or at a different time than use of brace 100 on the left foot.

For purposes of this disclosure, the term "substantially" is defined as "at least 95% of" and less than 100% of the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been disclosed with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

I claim:

1. A foot brace, comprising:
   a sole shaped to abut a plantar surface of a foot of a user;
   a cuff flexibly and fixedly connected to a rear portion of said sole, said cuff shaped to be disposed about an ankle of the foot of the user;
   a medial rail projection fixedly connected to a medial outer curvilinear edge of said sole at a front portion of said sole and a lateral rail projection fixedly connected to a medial lateral curvilinear edge of said sole at said front portion of said sole, said medial and lateral rail projections shaped to be disposed along a phalangeal region of the foot of the user, said medial and lateral rail projections each including an upper rail connected to said front portion of said sole by vertical rails, such that a hollow is formed between the vertical rails; and
   a pair of straps, connecting said medial and lateral rail projections to said cuff, thereby to connect said front portion of said sole to said cuff, said straps adapted to be tensioned to form an angle between said rail projections and said straps, thereby to secure the foot brace to the foot of the user, wherein said straps are selectably detachable from the cuff for removal of the foot brace from the foot of the user.

2. The foot brace of claim 1, further comprising a first flange and a second flange, both extending outwardly from said cuff along sides of said sole, said first flange extending along a lateral side of said sole and said second flange extending along a medial side of said sole, wherein said flanges are adapted to extend from said cuff toward a phalangeal region of the foot of the user.

3. The foot brace of claim 2, wherein a slit separates each of said first flange and said second flange from said sole.

4. The foot brace of claim 1, wherein said straps including a first fastener and said cuff includes a second fastener, the second fastener corresponding to the first fastener and being selectably connectable thereto and selectably detachable therefrom, such that said straps are selectably connectable to and detachable from said cuff by selectable connection of said first fasteners to said second fasteners.

5. The foot brace of claim 1, wherein tensioning of said straps decreases a distance between the front region of the sole and the cuff, thereby securing the brace on the foot of the user.

6. The foot brace of claim 1, adapted to be disposed within a shoe worn by the user, such that said sole engages a sole of the shoe, and said cuff engages an ankle portion of the shoe.

7. The foot brace of claim 1, further comprising a wire-bearing channel embedded into, and extending continuously through said sole and said cuff, said wire-bearing channel terminating in at least one bore extending through said sole or through said cuff.

8. The foot brace of claim 7, wherein a thickness of said sole or of said cuff, at said bore, is less than a thickness of said sole or of said cuff outside of said bore.

9. The foot brace of claim 7, further comprising conductive wiring electrically connected to a power source, the conductive wiring disposed within the wire-bearing channel and terminating in a mini vibration motor or in an electrode disposed within said bore, wherein, a working end of the mini vibration motor faces toward an upper side of said sole or and a working end of the electrode faces toward an inner side of said cuff, such that said electrode mini vibration motor is adapted to engage tissue of the user's foot and said electrode is adapted to provide a DC voltage to tissue of the user's calf.

10. The foot brace of claim 9, wherein the wire-bearing channel includes multiple branches, each terminating in a said bore, and wherein the conductive wiring includes multiple corresponding branches, each terminating in a said mini vibration motor or a said electrode, such that each of the multiple mini vibration motor and each electrode is disposed within one of said bores.

11. The foot brace of claim 9, wherein a first one of said bores, disposed at a first terminus of said wire-bearing channel is embedded in said sole, and a second one of said bores, disposed at a second terminus of said wire-bearing channel is embedded in said cuff.

12. A method of providing electrical stimulation to the foot of user using the foot brace of claim 9, the method comprising:
   placing a plantar surface of the foot of the user on a ventral surface of said sole;
   abutting said cuff of said foot brace to a calf muscle of the user; and
   tensioning said straps and connecting ends of said straps to said cuff, thereby to secure the foot brace about the foot of the user, such that said electrode engages tissue of the calf of the user; and activating said power source to provide electrical current to said electrode, via said conductive wiring, thereby to provide electrical stimulation to the tissue of the calf of the user.

13. The foot brace of claim 7, wherein said wire-bearing channel transversally extends along a majority of a longest dimension of a ventral surface of said sole and along a majority of a longest dimension of a surface of said cuff adapted to engage the leg of the user.

14. The foot brace of claim 7, wherein said wire-bearing channel includes a first branch terminating in a first bore and a second branch terminating in a second bore, the first and second branches being embedded within said cuff, wherein said first bore is disposed within a medial region of said cuff and said second bore is disposed within a lateral region of said cuff.

15. The foot brace of claim 7, wherein said wire bearing channel includes a plurality of branches embedded within said sole, each of said plurality of branches terminating at a corresponding bore extending through said sole.

16. The foot brace of claim 1, further comprising a pair of eyelet projection, each extending from and fixedly connected to one of said rail projections, said pair of eyelet projection being selectable connectable to and detachable from said straps for connection and detachment of said rail projections and said cuff.

17. The foot brace of claim 1, further comprising:

an exterior cuff fixedly connected to an upper portion of said cuff, wherein ends of said straps are reversibly connectable to said exterior cuff.

18. A method of donning the foot brace of claim 1 on the foot of a user, the method comprising:

placing a plantar surface of the foot of the user on a ventral surface of said sole;

abutting said cuff of said foot brace to a calf muscle of the user; and tensioning said straps and connecting ends of said straps to said cuff, thereby to secure the foot brace about the foot of the user.

* * * * *